(12) United States Patent
Gogly et al.

(10) Patent No.: US 8,303,948 B2
(45) Date of Patent: Nov. 6, 2012

(54) METHOD FOR TREATING SKIN WOUNDS

(75) Inventors: Bruno Gogly, Hondevilliers (FR); Bernard Coulomb, Igny (FR); Antoine Lafont, Paris (FR)

(73) Assignees: Universite Paris Descartes, Paris (FR), part interest; Institut National de la Sante et de la Recherche Medicale (INSERM), Paris (FR), part interest; Assistance Publique—Hopitaux de Paris, Paris (FR), part interest ( * ) Notice: Subject to any disclaimer, the term of this patent is extended or adjusted under 35 U.S.C. 154(b) by 612 days.

(21) Appl. No.: 12/376,856

(22) PCT Filed: Aug. 7, 2007

(86) PCT No.: PCT/IB2007/002264
§ 371 (c)(1),
(2), (4) Date: Feb. 9, 2009

(87) PCT Pub. No.: WO2008/017927
PCT Pub. Date: Feb. 14, 2008

(65) Prior Publication Data
US 2010/0166711 A1 Jul. 1, 2010

Related U.S. Application Data

(60) Provisional application No. 60/836,671, filed on Aug. 10, 2006.

(51) Int. Cl.
*A01N 63/00* (2006.01)
(52) U.S. Cl. ...................................................... 424/93.7
(58) Field of Classification Search ........................ None
See application file for complete search history.

(56) References Cited

U.S. PATENT DOCUMENTS

| 5,891,558 A | * | 4/1999 | Bell et al. | 428/218 |
| 2005/0203636 A1 | | 9/2005 | McFetridge | |
| 2006/0182725 A1 | * | 8/2006 | Marko et al. | 424/93.7 |
| 2008/0025954 A1 | * | 1/2008 | Lafont et al. | 424/93.7 |

FOREIGN PATENT DOCUMENTS

| DE | 10127933 | | 12/2002 |
| FR | 2872431 | | 1/2006 |
| WO | 9822154 | | 5/1998 |
| WO | 0182773 | | 11/2001 |
| WO | WO 2006013261 | * | 2/2006 |

OTHER PUBLICATIONS

International Search Report dated Nov. 11, 2008, in PCT application.

* cited by examiner

*Primary Examiner* — S. Devi
(74) *Attorney, Agent, or Firm* — Young & Thompson

(57) ABSTRACT

The present invention relates to a method for treating a skin wound in an individual, comprising applying to the skin wound of the individual a therapeutically effective quantity of gingival fibroblasts.

3 Claims, No Drawings

METHOD FOR TREATING SKIN WOUNDS

This application claims the benefit of prior U.S. provisional application 60/836,671 filed Aug. 10, 2006.

FIELD OF THE INVENTION

The present invention relates to a method for treating skin wounds, in particular by promoting or accelerating skin wound healing.

BACKGROUND OF THE INVENTION

Skin is a large organ, crucial for life, which protects the organism against environmental stresses, such as physical, chemical and mechanical stresses, and which prevents water loss. The complexity of skin notably arises from the association various tissues having different embryologic origins. While the barrier functions of skin depend on the epidermis, through the differentiation process of keratinocytes, skin homeostasis depends on the balance of multiple cellular and tissular interactions in which the dermis plays a key role.

Immediately after a skin injury has occurred, several events take place to repair the damaged tissue. Wound healing is a complex and dynamic process involving soluble mediators, blood cells, extracellular matrix components, and resident cells, including fibroblasts.

Briefly, the wound healing process includes three interactive phases: inflammation, granulation tissue formation and remodelling. This sequence of events aims at the recovering of tissue integrity and the restoration of its functions. The quality of the healing—which should ideally lead to an absence of scar and to the reestablishment of tissular function—is thus depending on a complex equilibrium.

In many species, the fetus possesses the unique ability to heal skin wounds without scar formation (Estes et al, (1994) *Differentiation* 56:173; Ferguson et al. (1996) *Plast. Reconstr. Surg.* 97:854), nevertheless adults will always present after-effects that can lead to functional disorders.

In some cases, problems occur during the wound healing process, leading to excessive scar development consecutive to an excessive extracellular matrix deposition (e.g. hypertrophic scars and keloids). In contrast, a disturbance in wound healing may also be characterized by poor healing or an absence of healing, as is notably observed in diabetes, and pressure, arterial or venous ulcers.

Hypertrophic scars and contraction features following burn wounds lead to functional troubles. The treatment for such wounds generally consists in the use of compressive dressings that will have to be kept during months or years. In most cases additional surgical operations will be necessary.

Furthermore, excessive scarring, poor healing or absence of healing, affect the quality of life of patients, but also represent a high cost.

Various treatments are currently used to try to restart the wound healing process in chronic wounds, such as the use of detersion, of growth factors, or of vacuum therapy. However, in many cases these treatments have proven unsatisfactory.

Thus, improvement of the functionality of "healed" area after wound closure is a first objective in the management of skin wounds. Besides, promotion and stimulation of the wound healing process in chronic wounds is another objective.

As such, grafting of cells or grafting of in vitro reconstructed tissues appears to be a promising field in the treatment of skin wounds.

In the frame of skin wound healing, the minimum requirement is to re-establish a barrier function to avoid infection and water loss. It is the horny layer of the epidermis (the product of terminal keratinocyte differentiation) that plays this role. However, although the barrier function depends on the epidermis, there is also a need to improve grafting by incorporating dermal tissue in order to promote the functionality of the engrafted zone.

Dermis neo-formation is an important step in wound healing since dermis accounts for a number of the mechanical properties of skin and promotes the formation and anchoring of a neo-epidermis, in particular through the activation of growth and differentiation of keratinocytes.

Dermal fibroblast grafting in the frame of the management of skin wounds has been shown to accelerate the formation of a neo-dermis and to improve the functionality of the grafted area (Coulomb et al. (1998) *Plast. Reconstr. Surg,* 101:1891-1903). This is notably due to the promotion of the synthesis of elastin which contributes to the mechanical properties of the skin. This improvement in dermis directly impacts on the organization and anchorage of epidermis.

Thus, in humans, a normal undulated dermo-epidermal junction is formed within one year of dermal fibroblast grafting in a skin wound whereas, in the absence of such a grafting, from 3 (in children) to 5 years (in adults) are required to obtained the same result.

However, the quality of wound healing, i.e. disappearance of wound marks (scar) and reestablishment of the functional properties of skin, is the result of a delicate balance and most of the time after-effects can not be prevented.

In addition, in situations such as large burns, dermal fibroblasts cannot be available in sufficient number.

As such, it is an object of the present invention to provide an advantageous alternative to the use of dermal fibroblasts in the management of skin wounds.

Other fibroblasts have been explored for their implication in wound healing. However, they have been found less efficient than dermal fibroblasts. For instance, fibroblasts of the adipose tissue although being similar to dermal fibroblasts in many respects (van der Bogaerdt et al. (2002) *Arch. Dermatol. Res.* 294:135-142) have proven less efficient than dermal fibroblast in promoting growth and differentiation of keratinocytes for the formation of an epidermis (Middelkoop (2005) *Int. J. Low Extrem. Wounds* 4:9-11).

Gingival fibroblasts are mesenchymal cells which are capable of migrating, adhering and proliferating within the soft connective tissues of the gum, thereby maintaining the integrity of the gingival tissue which is exposed to numerous aggressions, such as mechanical stresses, bacterial infections, or pH and temperature variations. Gingival fibroblasts are in particular described in Gogly et al., (1997) *Clin. Oral Invest.* 1:147-152; Gogly et al. (1998) *Biochem. Pharmacol.* 56:1447-1454; and Ejeil et al. (2003) *J. Periodontal.* 74:188-195.

Depending on environmental conditions, gingival fibroblasts are capable to modulate their phenotype, and to respond by proliferating, migrating, synthesising matrix components or matrix-related enzymes.

Gingival fibroblasts synthesise collagens (e.g. types I, III, V, VI, VII, XII) elastic fibers (oxytalan, elaunin and elastin), proteoglycans and glycosaminoglycans (e.g. decorin, biglycan), glycoproteins (e.g. fibronectin, tenascin). Simultaneously, gingival fibroblasts synthesise enzymes that are able to degrade the macromolecular compounds (matrix metelloproteinases; MMPs), but also enzymes inhibiting active forms of MMPs (Inhibitors of metalloproteinases; TIMPs). Gingival fibroblasts are thus important actors of extracellular matrix remodelling.

SUMMARY OF THE INVENTION

The present invention arises from the unexpected finding by the present Inventors that gingival fibroblasts could advantageously replace dermal fibroblasts in promoting the formation of a dermis in skin wounds.

Thus, the present invention relates to a method for treating a skin wound in an individual, comprising applying to the skin wound a therapeutically effective quantity of gingival fibroblasts.

The present application also relates to the use of gingival fibroblasts for the manufacture of a medicament intended for treating a skin wound.

In an embodiment of the above method and use, keratinocytes are also applied to the skin wound.

In another embodiment of the above method and use, at least one wound healing-activating compound is administered to the individual.

DETAILED DESCRIPTION OF THE INVENTION

Gingival Fibroblasts

Procedures for taking, culturing and preserving gingival fibroblasts are well known to the man skilled in the art and are particularly described in Naveau et al. (2006) *J. Periodontol.* 77:238-47.

Advantageously, gingival fibroblasts are easily sampled and cultured. Besides, gingival fibroblasts possess a high expansion rate.

Preferably, the gingival fibroblasts used in the method according to the invention are autologous, that is they are taken from the individual to the wounds of which they are intended to be applied. Preferably the individual is a mammal and more preferably a human. However, the gingival fibroblasts can also be allogenic, that is taken from another individual of the same species or heterologous, that is taken from another individual of another species.

Advantageously, gingival fibroblasts provide for an almost limitless source of autologous fibroblasts. Furthermore, in case of large burns, autologous gingival fibroblasts are usually still available, whereas, in contrast, sources of autologous dermal fibroblasts are scarce.

Skin Wound

As intended herein a "skin wound" relates to any rupture of the epidermis and/or the dermis.

Skin wounds according to the invention can be particularly selected from the group consisting of chronic wounds, pressure ulcers, venous ulcers, or skin burns.

Furthermore skin wounds according to the invention can also be surgical wounds, i.e. wounds voluntarily made during a surgical procedure. Such surgical wounds notably encompass wounds occurring in the course of plastic and reconstructive surgery or scar revision wounds (e.g. hypertrophic scars).

The plastic and reconstructive surgery procedures according to the invention can be of any type, e.g. breast surgery, abdominal surgery, nose surgery, ear surgery, or removal of skin defects. As intended herein, skin defects relate to an abnormal skin formation found in genetically predisposed individuals, or to the consequences of an abnormal skin development during embryogenesis, and notably comprise giant naevi, cheiloschisis, and keloids.

As intended herein "treating a skin wound" relates to the promotion, the acceleration, or the improvement of healing at the wounded site, i.e. the formation of a functional skin at the wounded site, and/or to the application of a gingival fibroblast-based functional skin substitute at the wounded sit.

As intended herein a "functional skin" relates to skin having in particular recovered its mechanical properties and its barrier function, with respect to non-wounded skin areas.

Application

As intended herein "applying" relates to the contacting or the grafting of gingival fibroblasts onto exposed tissues at the wound site.

The contacting or the grafting of the gingival fibroblasts onto exposed tissues at the wound site can be carried out according to any technique known the person skilled in the art.

The gingival fibroblasts can be directly deposited in the wound as a liquid or gel cell suspension, as a spray, or as a cell culture on a gel or solid medium.

Preferably, the cell culture of gingival fibroblasts is in a monolayer or tri-dimensional (3D) form. In particular, the cell culture can be a biocompatible lattice seeded and/or colonized by gingival fibroblasts.

As intended herein, a biocompatible lattice preferably relates to a lattice which does not induce rejection from the organism it is implanted in. More preferably a biocompatible lattice relates to a lattice which does not induce the formation of fibrosis. It is preferred that the biocompatible lattice used is bioresorbable, that is spontaneously degraded by the organism in which it is implanted, preferably after the lattice is no more useful for the cell culture. Preferably, the biocompatible lattice is made of one or several biopolymers, i.e. polymers which comprise at least one unit which can be found in living organisms. Materials for the constitution of the biocompatible lattice can in particular be selected from the group constituted of collagen, proteoglycan, fibrin, and chitin. Collagen Type I is preferred in the frame of the present invention, given its biocompatible and bioresorbable properties. Besides, the use of collagen is also advantageous since it can modulate fibroblast phenotype and promote an in vivo-like behaviour, in particular as regards differentiation, as described by Nusgens et al. (1984) *Collagen Rel. Res.* 4:351-364.

Lattices seeded and/or colonized by gingival fibroblast are designated as dermal equivalents in the Examples. General procedures for the implementation and implantation in skin wounds of dermal equivalents comprising gingival fibroblasts can be easily derived from Coulomb et al. (1998) *Plast. Reconstr. Surg,* 101:1891-1903 by the man skilled in the art.

The quantities of gingival fibroblasts to be applied to the wounds can be easily determined by the person skilled in the art depending on the mode of application. By way of example, for the preparation of a 10 cm×10 cm dermal equivalent based on a collagen lattice, approximately $8 \times 10^6$ individual gingival fibroblasts can be used to seed the lattice.

Keratinocytes

Keratinocytes are epidermal cells well known to the man skilled in the art which constitute the epidermis.

Keratinocytes used in the method according to the invention can be applied as individual cells or as cell cultures or tissue samples, such as skin biopsies.

As intended herein the keratinocytes can be applied prior to, simultaneously, and/or subsequently to gingival fibroblasts.

In particular, the keratinocytes can be directly applied to the wound once the gingival fibroblasts have been applied. Alternatively, the keratinocytes can be applied to the wound as a culture of cells grown on a culture of gingival fibroblasts. In an instance, after a dermal equivalent has been applied to a wound, keratinocytes are added thereon to form a skin equivalent in situ. In another instance a skin equivalent is prepared ex vivo by culturing keratinocytes onto a dermal equivalent and the whole skin equivalent is subsequently applied to the wound. General procedures for applying keratinocytes to skin wounds and for generating skin equivalents are described in Coulomb et al. (1998) *Plast. Reconstr. Surg.* 101:1891-1903.

Procedures for taking, culturing and preserving keratinocytes are well known to the man skilled in the art and are particularly described in Rheinwald at al. (1975) *Cell* 6:331-343.

Preferably, the keratinocytes used in the method according to the invention are autologous, that is they are taken from the individual to the wounds of which they are intended to be applied. Preferably the individual is mammal and more preferably a human. However, the keratinocytes can also be allogenic, that is taken from another individual of the same species or heterologous, that is taken from another individual of another species.

Keratinocyte are useful for the acceleration, or the improvement of healing at the wounded site, i.e. the formation of a functional skin at the wounded site, however they are particularly advantageous where application of a gingival fibroblast-based functional skin substitute at the wounded site is sought. In the latter case, it is preferred that the keratinocytes are autologous.

Wound Healing-Activating Compound

As intended herein a wound healing-activating compound relates to any compound which has the ability to promote, accelerate, or improve skin wound healing. Such compounds are preferably selected from the group constituted of growth factors and cytokines.

Within the frame of the method according to the invention such compounds can be administered prior to, simultaneously, and/or subsequently to the application of the gingival fibroblasts. The compounds can be administered by various administration routes such as the oral, intra-venous, intramuscular, or sub-cutaneous route. Alternatively, the compounds can also be directly applied to the wound.

EXAMPLES

Example 1

Sampling of Gingival Fibroblasts

Fibroblasts are recovered from biopsies either by using enzymatic treatment of the tissue sample or by migration of cells from tissue samples that have been placed to adhere on a cell culture substrate, in particular as described in Naveau et al. (2006) *J. Periodontol.* 77:238-47. Fibroblasts are then expanded on adapted culture media according to techniques well-known to the man skilled in the art.

Example 2

In Vitro Reconstruction of a Dermal Equivalent: Evaluation of Tissue Remodeling Promotion Gingival fibroblasts as obtained according to Example 1 are cultured in the presence of a tri-dimensional collagen lattice according to general procedures, such as the one described in Coulomb et al. (1998) *Plast. Reconstr. Surg.* 101:1891-1903 until the collagen fibrils of the lattice are contracted by the gingival fibroblasts to form a tissue-like structure, the dermal equivalent. The dermal equivalent is typically obtained after approximately 1 or 2 weeks of culture.

Preliminary results obtained by the Inventors indicate that gingival fibroblasts are more efficient than dermal fibroblasts in promoting tissue remodelling.

Example 3

In Vitro Reconstruction of a Skin Equivalent: Evaluation of Epidermalization Promotion A two-layered skin equivalent (epidermis+dermis) is produced by applying calibrated cutaneous biopsies obtained as described in Coulomb et al. (1986) *Br. J. Dermatol.* 4:157-168 as epidermal source, on a dermal equivalent constructed as described in Example 2.

This method is suitable for quantitatively evaluating epidermal formation by measuring epidermal surface. Epidermal formation is compared for dermal equivalents obtained with dermal fibroblasts (control) and gingival fibroblasts.

Preliminary results indicate that gingival fibroblasts are more efficient than dermal fibroblasts for promoting the growth and differentiation of an epidermis.

Example 4

In Vivo Wound Healing: Evaluation of Wound Closure Promotion

Rats are wounded by three muscle-deep cuts into which are respectively applied a control un-colonized collagen lattice, a dermal equivalent obtained with dermal fibroblasts and a dermal equivalent obtained with gingival fibroblasts (Example 2).

Wound healing speed and quality are monitored.

Preliminary results indicate that gingival fibroblasts are more efficient than dermal fibroblasts for promoting the formation of a neo-dermis.

All the cited bibliographic references are incorporated herein by reference.

The invention claimed is:

1. A method of accelerating or improving healing of a skin wound in an individual, consisting essentially of applying to the skin wound of the individual a quantity of isolated gingival fibroblasts.

2. The method of claim 1, wherein the gingival fibroblasts originate from the individual.

3. The method of claim 1, wherein the gingival fibroblasts are applied to the skin wound as a culture grown on a biocompatible lattice.

* * * * *